(12) United States Patent
Desiderio et al.

(10) Patent No.: US 8,277,940 B2
(45) Date of Patent: Oct. 2, 2012

(54) SCENT EMITTING PATCH AND/OR BANDAGE

(76) Inventors: Marcela N. Desiderio, Bedminster, NJ (US); Ernest D. Buff, Far Hills, NJ (US)

( * ) Notice: Subject to any disclaimer, the term of this patent is extended or adjusted under 35 U.S.C. 154(b) by 528 days.

(21) Appl. No.: 12/456,488

(22) Filed: Jun. 18, 2009

(65) Prior Publication Data

US 2010/0323155 A1    Dec. 23, 2010

(51) Int. Cl.
*B32B 5/16* (2006.01)
*B32B 9/04* (2006.01)
*B32B 3/10* (2006.01)
*B05D 7/04* (2006.01)
*B05D 5/10* (2006.01)
*B32B 3/12* (2006.01)
*B32B 3/24* (2006.01)
*B32B 3/30* (2006.01)
*B32B 37/00* (2006.01)

(52) U.S. Cl. .......... 428/354; 428/68; 428/131; 428/137; 428/138; 428/156; 428/166; 428/172; 428/174; 428/178; 428/195.1; 428/220; 428/343; 428/355 R; 428/905; 602/41; 602/42; 602/52; 602/54; 602/58; 602/59; 156/145

(58) Field of Classification Search .................. None
See application file for complete search history.

(56) References Cited

U.S. PATENT DOCUMENTS

| | | | | |
|---|---|---|---|---|
| 2,626,833 A | * | 1/1953 | Valentine | ............... 239/56 |
| 3,896,995 A | * | 7/1975 | Lelicoff | ............... 239/36 |
| 4,212,296 A | * | 7/1980 | Schaar | ............... 602/42 |
| 4,277,024 A | * | 7/1981 | Spector | ............... 239/36 |
| 4,283,011 A | * | 8/1981 | Spector | ............... 239/36 |
| 4,285,338 A | * | 8/1981 | Lemelson | ............... 602/58 |
| 4,465,232 A | * | 8/1984 | Field | ............... 239/36 |

(Continued)

FOREIGN PATENT DOCUMENTS

JP        11056997 A   *   3/1999

(Continued)

OTHER PUBLICATIONS

Machine Translation of KR 2003048730 A, Jun. 2003.*

(Continued)

*Primary Examiner* — David Sample
*Assistant Examiner* — Jeff Vonch
(74) *Attorney, Agent, or Firm* — Ernest D. Buff; Ernest D. Buff & Assoc. LLC; Margaret A. LaCroit (57) ABSTRACT

A scent emitting patch remains securely attached to the skin of a wearer and is appointed for controlled release of scents. The patch is constructed having an external top layer and backing layer with a skin-contacting portion. The skin-contacting segment contains an adhesive. At least one reservoir comprising pockets or microcapsules containing a scent is disposed in at least one portion of the backing layer. These pockets or microcapsules are operative to rupture upon application of pressure or scratching by the patch wearer. Upon rupture, scent is delivered to the skin to emit aroma. Pockets containing the scent are formed in the backing layer. Microcapsules, if present, are preferably incorporated in the adhesive. A plethora of aromas are provided in the form of a perfume or cologne and correlating shapes can be used to form the patch. Scent is released at the skin-contact interface when pressure is applied ruptures the pockets or microcapsules, permitting controlled release at the wearer's election.

13 Claims, 5 Drawing Sheets

U.S. PATENT DOCUMENTS

| | | | | |
|---|---|---|---|---|
| 4,515,703 A | * | 5/1985 | Haq | 15/104.93 |
| 4,654,256 A | * | 3/1987 | Doree et al. | 428/304.4 |
| 4,776,331 A | * | 10/1988 | Simjian | 602/43 |
| 4,874,129 A | * | 10/1989 | DiSapio et al. | 239/36 |
| 4,880,690 A | * | 11/1989 | Szycher et al. | 442/304 |
| 5,071,704 A | * | 12/1991 | Fischel-Ghodsian | 428/354 |
| 5,395,047 A | * | 3/1995 | Pendergrass, Jr. | 239/56 |
| 5,399,404 A | * | 3/1995 | Laughlin et al. | 428/41.3 |
| 5,951,534 A | * | 9/1999 | Cummings et al. | 604/359 |
| 6,162,454 A | * | 12/2000 | Ahr et al. | 424/411 |
| 6,162,457 A | | 12/2000 | Martz | 424/448 |
| 6,613,953 B1 | * | 9/2003 | Altura | 602/43 |
| 6,723,671 B2 | * | 4/2004 | Zolotarsky et al. | 442/417 |
| 6,747,183 B2 | * | 6/2004 | Siegwart et al. | 602/58 |
| 6,769,428 B2 | | 8/2004 | Cronk et al. | 128/200.24 |
| 6,787,679 B1 | * | 9/2004 | Cantor | 602/41 |
| 6,921,844 B2 | | 7/2005 | Cantor | 602/41 |
| 6,991,842 B2 | * | 1/2006 | Hurwitz | 428/71 |
| 7,011,093 B2 | | 3/2006 | Anderson et al. | 128/206.12 |
| D580,593 S | | 11/2008 | Huntington | D28/4 |
| 2007/0055216 A1 | * | 3/2007 | Rashid | 604/544 |
| 2007/0249981 A1 | * | 10/2007 | Hurwitz et al. | 602/58 |
| 2009/0148483 A1 | * | 6/2009 | Rashid | 424/405 |

FOREIGN PATENT DOCUMENTS

| | | | | |
|---|---|---|---|---|
| JP | 2000262599 A | * | 9/2000 | |
| JP | 2002345942 A | * | 12/2002 | |
| JP | 2005047134 A | * | 2/2005 | |
| JP | 2007000297 A | * | 1/2007 | |
| KR | 2003048730 A | * | 6/2003 | |

OTHER PUBLICATIONS

English Abstract for JP 11056997 A, Mar. 1999.*
English Abstract for JP 2000262599 A, Sep. 2000.*
English Abstract for JP 2002345942 A, Dec. 2002.*
English Abstract for JP 2005047134 A, Feb. 2005.*

* cited by examiner

SCENT EMITTING PATCH AND/OR BANDAGE

BACKGROUND OF THE INVENTION

1. Field of the Invention

The present invention relates to scent emitting patches and/or bandages; and more particularly to bandages and/or patches designed to release a preselected scent on command.

2. Description of the Prior Art

Perfume sprays and lotions are frequently applied to the skin so that a pleasant scent is emitted. It is nearly impossible for a user to apply the optimal amount of perfume for all day wear as the perfume aroma dissipates. Frequently, users administer a liberal application of perfume in the morning. An overly potent fragrance emanates therefrom. However, the fragrance becomes diluted to nearly non-existent by the end of the day. Release of scent from perfumes currently applied is not readily controlled by the wearer. As a perfumed scent dissipates, the user must reapply the perfumed spray, oil or lotion.

Bandages are well known in the art and are used for various medical applications and sports protection. Sterile bandages marketed under well-recognized trade names, such as 'Band-Aid', 'Cural' and the like, provide secure attachment of the bandage's adhesive portion to bare skin adjacent to a wound. A sterile wound-covering pad is appointed to come into contact the wound. Few bandages afford scent dispersing mechanisms. Those that do provide a bandage wherein an adhesive portion has fragrance portions disposed therein. A release cover is releasably secured to the adhesive portion. When removed, the cover allows for release of a scent associated with the fragrance portions Such a bandage is disclosed in U.S. Pat. Nos. 6,787,679 and 6,921,844 to Cantor. These bandages fail to provide release of the scents on command by pressing the external side of the bandage to release perfume. Instead, scent is released when a release cover is removed, exposing the fragrance portions.

Various nasal dilators and strips have been devised that include microencapsulated fragrances and methods for emitting aromas when wearing the nasal dilators. The nasal dilators are adhesively applied external nasal strips and dilators containing medications and fragrances including an elongated substrate, with or without a dilating component or portion, having top and bottom surfaces and a pressure-sensitive adhesive disposed on the bottom surface with a cosmetic fragrance, an aromatic medication and/or transdermal medication disposed on the strips or dilators. Such devices can be found in U.S. Pat. No. 7,011,093 to Anderson, et al. and U.S. Pat. No. 6,769,428 to Cronk, et al. These nasal dilators do not provide perfume bandages or patches with pressure sensitive release of scents that can be applied anywhere on the body. Rather, these nasal dilators are limited to use on a person's nose and are constructed for aiding breathing through the nose.

Personal perfume application methods and systems have been suggested for fragrance emitting patches. One type provides a fragrance emitting patch that is worn with the fragrance emitting side facing the skin of the user with the adhesive side adhered to the user's clothing so that the fragrance contacts the body oils of the user and a muted odor is emitted. Other devices provide similar patches that are adhered to articles of clothing in general. Such devices are disclosed in U.S. Pat. No. 6,162,457 to Martz, U.S. Design Pat. No. D580,593 to Huntington, U.S. Pat. No. 6,723,671 to Zolotarsky, et al., and U.S. Pat. No. 4,283,011 to Spector. These devices do not provide for controlled release of the scent. Rather the scent is disseminated throughout the day as the fragrance contacts the body and rubs against the skin.

Notwithstanding the efforts of prior art workers to manage scent emission, there exists a need in the art for a scent emitting bandage or patch that adheres to the skin securely and releases scent when pressure is applied to an exterior surface thereof. There also remains a need in the art for a flexible bandage or patch that is designed to release a preselected scent on command. Further, there remains an art recognized need for a bandage or patch having an adhesive into which are admixed a plurality of microcapsules or micro pockets that contain a perfumed scent; which microcapsules or micro pockets fracture upon application of pressure to the exterior surface of the bandage, triggering release of the perfumed scent.

SUMMARY OF THE INVENTION

The present invention provides a flexible scent emitting patch or/and bandage that adheres to the skin and readily disperses a perfumed scent or fragrance upon demand. Controlled release of the scent is achieved by providing a perfume housed within a plurality of reservoirs constructed as microcapsules or micro pockets integrated within the patch. Application of pressure to an exterior surface of the patch causes the microcapsules or pockets to fracture and the perfume to release onto the local skin. Preselected scents are designed to be released on command. A plurality of the microcapsules or micro pockets containing a perfume or other scent emitting medium are admixed with an adhesive on the underside of the patch so that substantially direct contact of the perfume with the skin is achieved. Accordingly, the scent of the perfume comingles with the individual's body oils to yield a rounded fragrant scent when the perfume is released.

Perfumes used in the scent emitting patch can be matched or made compatible with an established perfume, enabling the patch to be sold as part of a product line carried by trade names such as Christian Dior, Channel, or the like. Scents geared toward children can be provided wherein a sharp odor is emitted that emulates preselected scents like strawberries, flowers, jelly beans, burned rubber, or other fun scents like dragon's breath, for example. Correspondingly, the shape of the patch or bandage can be designed to emulate a strawberry, flower, jelly bean, doll, dragon, racing car, etc. with the scents designed to be compatible with these designs.

Generally stated, the patch may be constructed as a scent emitting patch, or as a scent emitting bandage. The patch has an adhesive layer comprising at least one pocket (and preferably a plurality of pockets) or a plurality of microcapsules of a scent—such as a perfume or fragrance—that is readily released when the user desires. The scent may be released by the application of pressure to the external surface or external top layer of the patch or by scratching the external surface or pressing. This application of pressure causes the pockets or microcapsules to break, releasing the scent. Due to the arrangement of the microcapsules within the back layer, the scent is released at the interface between the skin and the back layer or a portion of the skin-contacting layer enabling the scent to combine with and interact with the user's oils and body scent.

The backing layer of the bandage may be provided with pockets that contain the scent. Alternatively, the scent may be contained in capsules or microcapsules that are applied concurrently with the adhesive layer of the patch, or located within a separate portion of the back layer of the patch. The overall volume of the pockets or microcapsules determines the amount of the scent or perfume available. Once released, the scent is spread to an area at the skin-contact interface. The pockets included in the backing layer may be spaced apart, and the size of the pockets will be dependent on the amount of scent to be dispersed and the size of the patch. However, when microcapsules are used, they tend to be distributed more uniformly and are more closely spaced, since each of the microcapsules contains only a small amount of the scent.

The scent is contained in pockets within the backing sheet in a first embodiment of the invention. In a second embodiment of the invention, the scent is contained in microcapsules that are incorporated in the adhesive layer. In the first embodiment, the backing sheet is fabricated from two polymeric sheets. The first polymeric sheet is embossed to create the pockets and filled with the scent. The shape of the pockets may be spherical, cylindrical or elongated, or any suitable shape. The pockets may be interconnected to form a continuous single pocket such as an interconnected channel. The pockets may be arranged to have a decorative shape such as a picture frame that is within a short, approximately ⅛ inch to 5/16 of an inch, distance from the edges of the skin-contacting portion. The central portion of the picture frame may have one or more x-shaped interconnected pockets providing a decorative appearance. The patch can be shaped in a plethora of shapes to represent objects and/or characters. The scent may correlate with the shape of the patch. For example, where the patch is shaped as a flower, the scent could be a floral perfume or fragrance. Or where the patch is shaped as a strawberry, the scent could be that of a strawberry or fruit. The second polymeric sheet, which is substantially thinner, is bonded to the first sheet with embossed and ingredient filled pockets thereby encapsulating the scent in the backing sheet. Applying pressure to or scratching the outer surface or exterior top layer of the backing sheet breaks the pockets on the thinner second polymeric sheet, thereby releasing the scent at the skin-contact interface.

The glue used for attachment to the skin comprises acrylic based, dextrin based, and urethane based adhesives as well as those based on natural and synthetic elastomers. The adhesives may also include amorphous polyolefins including amorphous polypropylene, such as HL-1308 from HB Fuller or Rextac RT 2373 from Huntsman (Odesssa, Tex.). Water resistant adhesives include polymerization reaction product two alkyl acrylate or methacrylate ester monomers such as butyl acrylate, ethyl acrylate, 2-ethylhexyl acrylate, isooctyl acrylate, isononyl acrylate, isodecyl acrylate, methyl acrylate, methylbutyl acrylate, 4-methyl-2-pentyl acrylate, sec-butyl acrylate, ethyl methacrylate, isodecyl methacrylate, methyl methacrylate with ethylenically unsaturated carboxylic acid, a vinyl lactam, and including a crosslinking agent. Preferably, oil scents are not used where it is desired that the patch be capable of continued wear after rupture of at least some of the microcapsules or pockets as the oil may inactivate the adhesive. Where oil scents are used, the patch adhesive may become degraded after the microcapsules or pockets are ruptured, facilitating easy removal of the patch.

The scent may be contained in pockets of the embossed backing layer. The spreadability of the scent is determined by its volume, viscosity and surface tension. Since pockets contain a larger volume of the scent, they can be spaced apart further based on the volume. The volume is generally in the range of 0.01 cc to 0.5 cc and the spacing between the pockets is in the range of 0.01 cm to 0.2 cm. Microcapsules are generally small. They contain only a small quantity of scent and can only spread over a small distance, approximating a few times the diameter of the microcapsule. These microcapsules may be added to the adhesive and are nearly uniformly dispersed in the adhesive layer. Therefore, the appropriate measure is the relative volume of the scent as compared to the volume of the adhesive. This ratio is typically in the ratio of 5 to 20%.

BRIEF DESCRIPTION OF THE DRAWING

The invention will be more fully understood and further advantages will become apparent when reference is had to the following detailed description of the preferred embodiments of the invention and the accompanying drawings, in which:

FIG. 4b is a cross-sectional view of the bandage embodiment of FIG. 4a;

FIG. 5b is a schematic diagram of a cross sectional view of the bandage embodiment of FIG. 5a.

DETAILED DESCRIPTION OF THE INVENTION

The present invention provides a patch or bandage that is well bonded to the skin, and retains scent emitting microcapsules or pockets providing controlled release of the scent/perfume. The microcapsules or pockets can be readily ruptured or fractured to release the scent or perfume onto the user's skin with the application of pressure, such as by scratching the outer surface or external top layer. This scratching action or application of pressure breaks pockets or microcapsules that release the scent or perfume at the skin-contact interface.

Where the patch is provided as a bandage, the bandage typically comprises a backing layer with a central region for attachment to an absorbent pad and two end portions which carry an adhesive coating that contacts the skin of the user and attaches the bandage. The absorbent pad that contacts the wound surface is attached to the central portion of the backing layer by hot melt glue or conventional strong glue. Examples of suitable adhesives include those based on styrenic block copolymers and tackifying resins such as HL-1491 from HB-Fuller Co. (St. Paul Minn.), H-2543 from ATO-Findley (Wawatausa, Wis.), and 34-5534 from National Starch & Chemical (Bridgewater, N.J.). Ethylene copolymers, including ethylene vinyl acetate copolymers, may also be used as adhesives to bond the absorbent pad to the backing sheet. This adhesive retains the absorbent pad on the backing strip and has little or no effect on peeling of the bandage from the skin. Bandages, which retain a splint or are used for sports purposes do not generally, contain this absorbent pad attached to the central portion of the backing layer.

The end portions of the backing layer are coated with an adhesive coating that permits the attachment of the bandage to the skin. There are specific requirements for the adhesive coating composition. First, it must be able to contact the skin for a prolonged period of time without irritating the skin. The adhesive must have sufficient strength to retain the bandage against the skin securely, thereby holding the absorbent pad in contact with the wound, or retaining a splint. The adhesive cannot be rigid and must be flexible enough to allow movement of the skin. Brittle adhesives crack and fail easily. Technical improvements in this area have focused on improving the quality of the adhesive and strengthening its bond to the skin. The adhesive must also exhibit a balance between its shear properties and adhesion properties, which are inversely related. In a "wet flex" performance test for adhesive bandages, when applied to fingers, the failure modes are: (i) "flagging", that is, when the overlapped bandage pops open due to a failure to adhere to itself; and (ii) "ring off", which occurs when the overlapped bandage loses adhesion to the skin and slips off. Typically, very soft, highly tacky adhesives exhibit low shear strength, while hard adhesives are only slightly tacky and exhibit high shear strength. An adequate degree of adhesive and shear properties are required so that no adhesive residue remains when the bandage is removed from the skin of the wearer.

The glue used for attachment of the bandage to the skin comprises acrylic based, dextrin based, and urethane based adhesives as well as those based on natural and synthetic elastomers. The adhesives may also include amorphous polyolefins including amorphous polypropylene, such as HL-1308 from HB Fuller or Rextac RT 2373 from Huntsman (Odesssa, Tex.). Water resistant adhesives include the polymerization reaction product of (i) two alkyl acrylate or methacrylate ester monomers such as butyl acrylate, ethyl acrylate, 2-ethylhexyl acrylate, isooctyl acrylate, isononyl acrylate, isodecyl acrylate, methyl acrylate, methylbutyl acrylate, 4-methyl-2-pentyl acrylate, sec-butyl acrylate, ethyl methacrylate, isodecyl methacrylate, and methyl methacrylate with (ii) ethylenically unsaturated carboxylic acid, (iii) a vinyl lactam, and (iv) a crosslinking agent. Improvement in adhesive strength properties have resulted in adhesives that bond well to the skin and do not peel off or fall off even when the bandage becomes wet.

Prior art workers have provided personal perfume application methods and systems wherein a patch is worn on a piece of clothing with the adhesive side adhered to clothing while the fragrance emitting side rubs against the skin. These approaches do not provide for controlled release of the scent and instead provide that the scent is disseminated throughout the day as the fragrance contacts the body and rubs against the skin. At the early day or time of application, these patches have a stronger emission of the scent, however by the end of the day or after merely a few hours the scent is dissipated and the amount of emission becomes faint or non-existent. These approaches deteriorate the scent, reducing its performance and fail to provide the scent at a desired intensity when the user desires or feels they need enhanced fragrance.

It has been surprisingly found that utilizing a plurality of microcapsules or pockets constructed within the back layer of the patch provides a controlled release of a scent, particularly a perfume. The capability of controlling release of a scent allows a user to release more or less of the fragrance when needed. Therefore, rather than a scent dissipating throughout the day, the user of the scent emitting patch of the present invention can trigger release of scents throughout the day as desired by simply scraping or applying pressure to the patch.

Figure 1A:
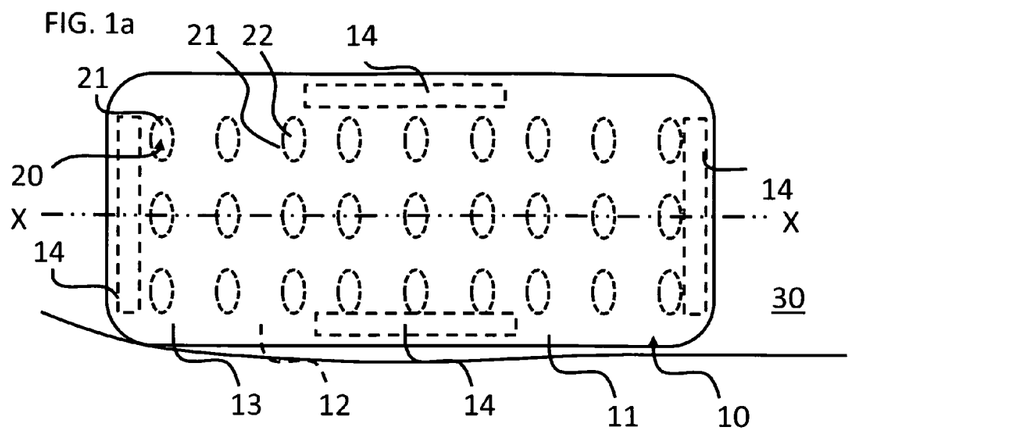
FIG. 1a is a top view of an embodiment of the scent emitting patch adhered to a skin surface wherein a plurality of pockets housing a perfume or other preselected scent is integrated in the back layer of the patch.
Figure 1B:
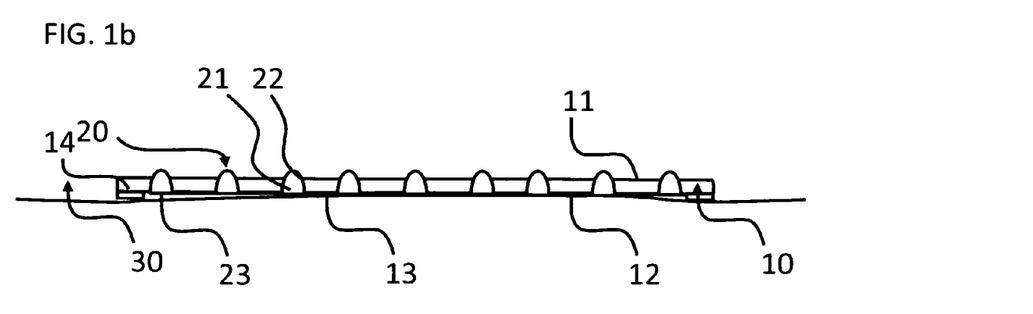
FIG. 1b is a cross-sectional view of the patch of FIG. 1a taken along line X-X prior to the application of force and rupturing of the pockets.
Figure 1C:
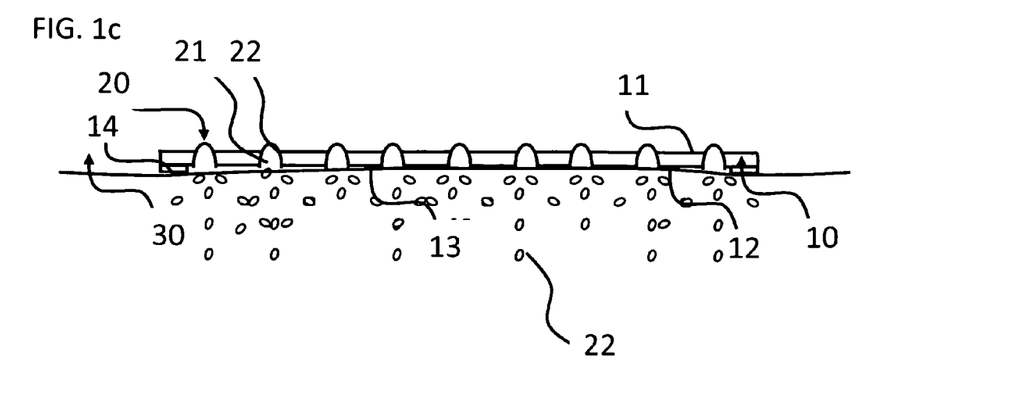
FIG. 1c is a cross-sectional view of the patch of FIG. 1a taken along line X-X after application of force and rupturing of the pockets to release the perfume housed therein onto the skin.

FIGS. 1a-1c illustrate views of a first embodiment of the scent emitting patch adhered to a skin surface wherein a plurality of pockets housing a perfume or the like is integrated in the back layer of the patch. Specifically, FIG. 1a is a top view of the scent emitting patch adhered to a skin surface, FIG. 1b is a cross-sectional view taken along line X-X prior to the application of force and rupturing of the pockets, and FIG. 1c is a cross-sectional view taken along line X-X after application of force and rupturing of the pockets to release the perfume housed therein onto the skin.

Referring to FIGS. 1a-1c, the scent emitting patch, shown at 10, is constructed having an external top layer 11 and a backing layer 12. Backing layer 12 includes a skin-contacting segment 13 appointed for contact with skin 30 of a patch wearer. Skin-contacting segment 13 preferably substantially makes-up the backing layer 12, as herein shown, so that the surface area of the backing layer 12 which is skin-contacting is approximately 100%. However, where the patch is constructed as a bandage (as discussed hereinafter), the skin-contacting portion is less, since accommodation must be made for a central wound-contacting absorbent pad. At least one reservoir 20 containing a scent 22 is disposed in the backing layer 12. Reservoir 20 may be constructed as at least one pocket integrated within the backing layer 12. Preferably, reservoir 20 is provided as a plurality of reservoirs 20, which are constructed as pockets 21 as shown in FIG. 1a. These pluralities of pockets 21 are integrated within the backing layer 12. In a second embodiment, pluralities of reservoirs are provided constructed as microcapsules disposed on the backing layer as illustrated in FIGS. 3a, 3b and 5a, 5b.

The reservoirs 20 or pockets 21 as herein shown, are operative to rupture upon application of pressure or scratching by the patch wearer, thereby releasing the scent 22. Upon release, scent 22 is delivered to the skin 30 of the patch wearer for emanating the scent 22. The scent is preferably a perfume composed of a mixture of fragrant essential oils and aroma compounds, fixatives, and solvents used to give the human body, animals, objects, and living spaces a "pleasant" smell. Perfume types to be utilized preferably include: perfume extract (15-40% aromatic compounds); eau de parfum, parfum de toilette (10-20% aromatic compounds); eau de toilette (5-15% aromatic compounds); eau de cologne (3-8% aromatic compounds; and splash and after shave (1-3% aromatic compounds).

Figure 2:
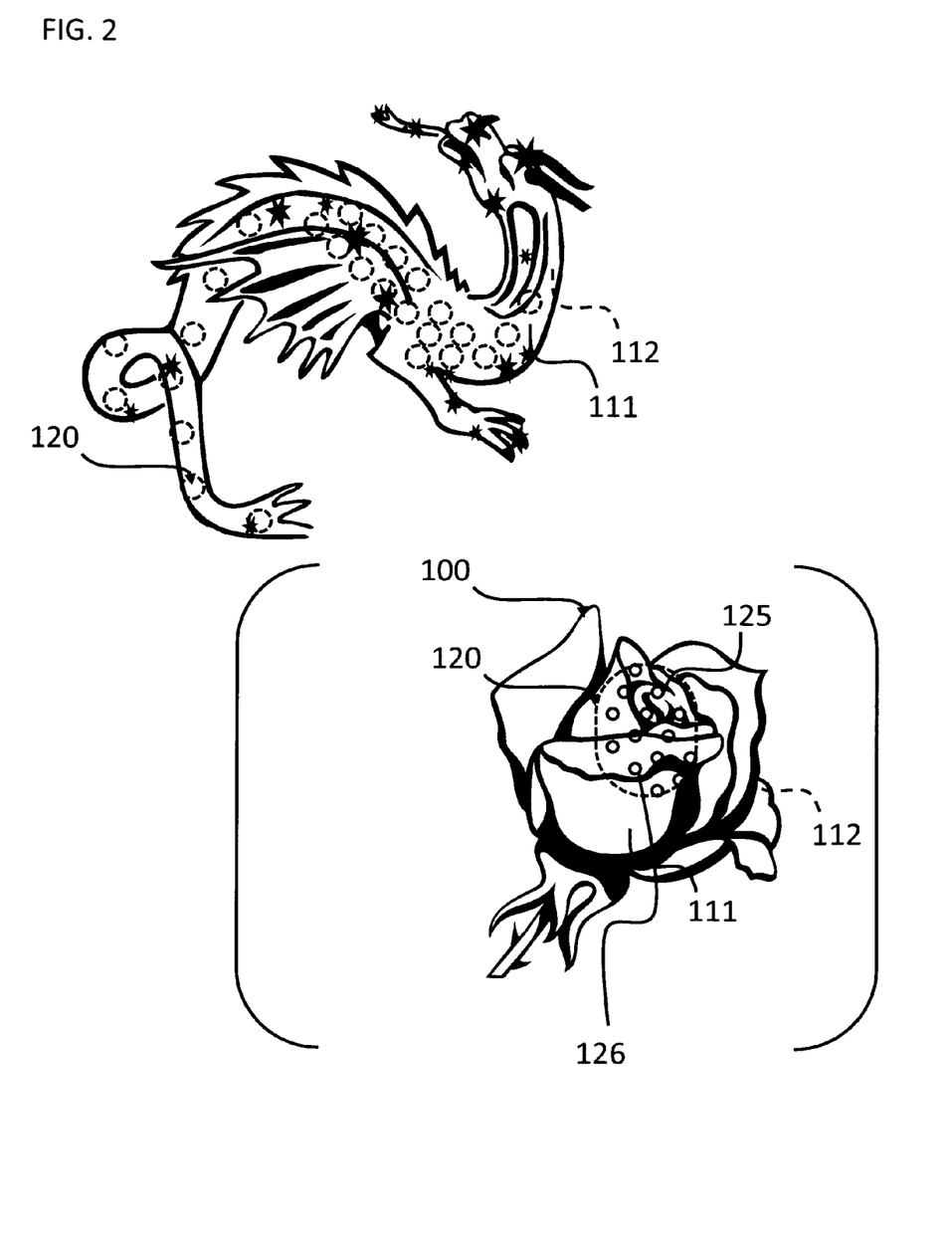
FIG. 2 is a top view of various shaped scent emitting patches.

As fragrance compounds in perfumes will degrade or break down if improperly stored in the presence of light, preferably the external top layer 11 is opaque to limit light exposure to the reservoirs 20 or, as herein, pockets 21 housing the scent 22. External top layer 11 may be flesh colored so that the patch 10 is barely discernible or camouflaged on the skin. If external top layer 11 is transparent, then storage of the patch 10 before use is preferably done to limit light exposure during storage. Further, external top layer 11 may include at least one portion having a plurality of apertures or perforations integrated therein. These apertures or perforations are located in alignment with each of the reservoir/reservoirs 20 (herein shown as pockets) containing the scent 22 disposed in the backing layer 12, as illustrated in FIG. 2 (via rose 100). These apertures or perforations allow the skin to breath under the patch, as well as facilitating in the emission of the scents after the pockets or microcapsules are ruptured.

At least one portion of the skin-contacting segment 13 of backing layer 12 contains an adhesive, herein shown as portions 14. Preferably pluralities of portions of the skin-contacting segment 13 of backing layer 12 contain an adhesive. These plurality of portions are preferably located along an outer perimeter of the back layer 12 as shown in FIG. 1a when the scent 22 is a perfume having a high oil concentration that may be capable of breaking down the adhesive 14, and/or to provide easy flow of the liquid perfume or scent 22 onto the skin 30 as the pocket 21 is ruptured. For example, where the adhesive is selected from a group comprising acrylic based, dextrin based, and urethane based adhesives, and adhesives based on natural and synthetic elastomers, the adhesive may be subject to break-down in the presence of certain oils. Where this is the case, a perfume having a lower aromatic concentration or lower oil concentration may be desired. Alternatively, the patch 10 may desired to be removed after a single dosage or release application, and in which case deterioration of the adhesive 14 will actually be desirable for ouch-free removal. For ready flow of the scent 22 when the pockets 21 are ruptured, the desirable spacing of the adhesive 14 is that located along two parallel side perimeters of the back layer 12 as shown in FIG. 1a. Such spacing may be more desired when scent 22 is of a larger volume and needs room to flow onto the local skin 30 when reservoirs 20 are constructed as pockets 21.

A single reservoir 20 may be provided, or preferably, pluralities of reservoirs 20 are provided that are individually separated, or interconnected with one another. Preferably, the reservoir 20 is disposed within the skin-contacting segment 13 of the backing layer 12 so that the scent 22 is directly delivered to the skin 30. The reservoirs 20 containing the scent 22 may be disposed in the adhesive-containing portions 14 of the backing layer 12. As shown herein, skin-contacting segment 13 of the backing layer 12 is preferably embossed with a plurality of reservoirs 20 constructed as pockets 21, filled with the scent 22 and sealed with a second polymeric layer 23 prior to the application of the adhesive 14. Second polymeric layer 23 ruptures upon the application of force, releasing scent 22 or perfume onto the skin 30. Reservoirs 20/pockets 21 preferably have a volume ranging from about 0.01 cc to 0.5 cc and are spaced apart by a distance ranging from about 0.01 cm to 0.2 cm. Preferably, reservoirs 20/pockets 21 contain about 5 to 20 volume percent of the scent 21 as compared to the volume of the adhesive 14.

In this first embodiment of the invention the reservoirs are constructed as pockets that encapsulate the scent in the backing layer of the patch. This is conveniently accomplished by preparing the backing layer as a two polymeric sheet construction, wherein the first polymeric sheet is embossed to create pockets. These embossing shapes may be spherical, cylindrical or elongated and may be individually separated or interconnected. The pockets are filled with a liquid scent, preferably a perfume. A second polymeric sheet, which is generally thinner and has low strength properties, is spread over the first polymeric sheet, covering the pockets. It is then heat sealed or sealed by other methods to encapsulate the scent. When pressure is applied to the outer surface/external top layer of the backing layer, or the external top layer is scratched, the pockets at the second polymeric sheet rupture, releasing the scent/perfume at the skin-contact interface. This release provides for easy, controllable emission of the scent so that the wearer can give him/herself a boost of aroma when it suits the convenience of the wearer.

When a pocket breaks, it releases the scent. How far the scent or perfume spreads is a function of the volume of scent contained in the pocket, and its viscosity and surface tension, or wetting characteristics. High viscosity oils spread slowly. Reduced surface tension promotes spreadability. Surfactants reduce the surface tension and improve spreading capability. Viscosity may be increased by the addition of thickeners. The pockets are generally larger and therefore contain a larger volume of the scent, and can spread the scent over a larger distance. Typically the pockets may have a volume of 0.01 cc to 0.5 cc and the spacing between the embossed pockets in the backing layer may be 0.01 cm to 0.2 cm. The scent or perfume composition should be contained in the pockets or microcapsules indefinitely without chemical reaction or dissolution. The second polymeric sheet encasing the pockets may include a layer of polyethylene, which is immune to dissolution by oily compositions.

Perfumes used in the scent emitting patch can be matched or made compatible with an established perfume, enabling the patch to be sold as part of a product line carried by trade names such as Christian Dior, Channel, or the like. Scents geared toward children can be provided wherein a sharp odor is emitted that emulates preselected scents such as strawberries, flowers, jelly beans, burned rubber, or other fun scents like dragon's breath, for example. Correspondingly, the shape of the patch or bandage can be designed to immolate a strawberry, flower, jelly bean, doll, dragon, racing car, etc. with the scents designed to be compatible with these designs. For example, the scent may be fashioned with a sharp odor emulating burned rubber, and used to fill microcapsules or micro pockets in a bandage or band aid having the shape of a racing car. FIG. 2 is a top view of various shaped scent emitting patches having an external top layer 111 and a backing layer 112 with at least one reservoir 120, or a plurality of reservoirs 120 containing a scent disposed therein constructed as pockets or microcapsules integrated within the backing layer 112. Where fewer reservoirs 120 are provided, the reservoir preferably holds a larger volume of scent. Further, as shown at 100, via a shape of a rose, the external top layer 111 may include at least one portion 125 having a plurality of apertures 126 integrated therein located in alignment with each of the reservoirs 120 (herein shown as a pocket) containing the scent disposed in the backing layer 112.

Figure 3A:
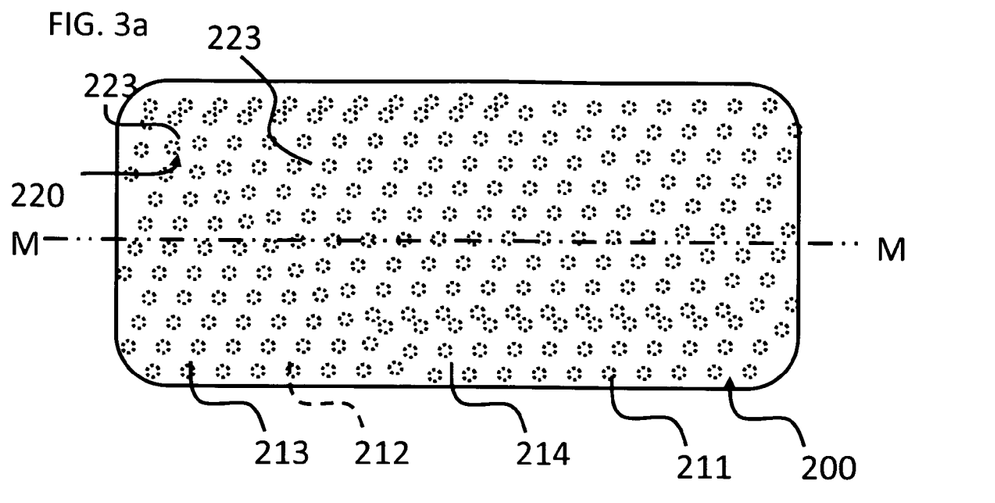
FIG. 3a is a top view of an embodiment of the scent emitting patch wherein pluralities of microcapsules housing a perfume or the like are admixed with the adhesive in the back layer of the patch.
Figure 3B:
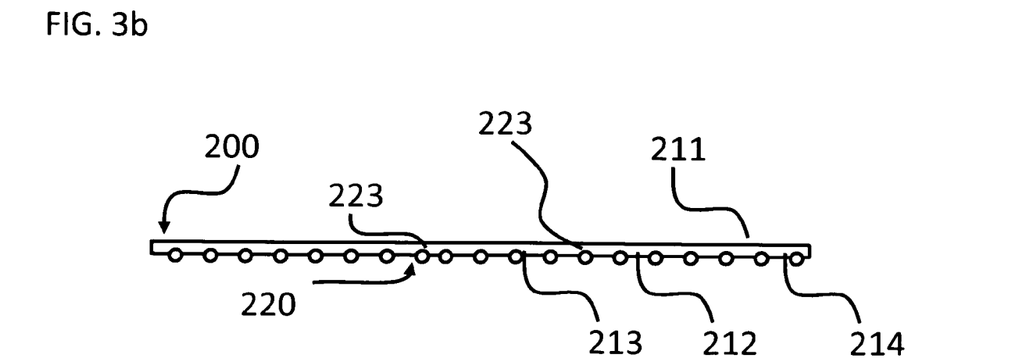
FIG. 3b is a cross-sectional view of the patch of FIG. 3a taken along line M-M prior to the application of force and rupturing of the pockets.

FIG. 3a is a top view of an embodiment of the scent emitting patch wherein pluralities of microcapsules housing a perfume or the like are admixed with the adhesive in the back layer of the patch, shown generally at 200. FIG. 3b is a cross-sectional view of the patch of FIG. 3a taken along line M-M prior to the application of force and rupturing of the pockets. In this second embodiment a standard backing layer commonly composed of a polymer or other fabricate, as employed with bandage constructions, is used. The adhesive that is applied to the skin contacting end portions of the backing layer includes microcapsules that contain the scent or perfume. The adhesive bonds to the skin effectively and the patch is retained on the skin. When release of the scent is desired, the wearer applies pressure to the adhesive portion of the patch, or scratches this region. The microcapsules rupture, releasing the scent or perfume at the skin-adhesive interface. With this release, there is effected effortless controlled delivery of the scent.

Referring to FIGS. 3a and 3b, the scent emitting patch, shown at 200, is constructed having an external top layer 211 and a backing layer 212. Backing layer 212 includes a skin-contacting segment 213 appointed for contact with skin of a patch wearer. Skin-contacting segment 213 preferably substantially makes-up the backing layer 212, as herein shown, so that the surface area of the backing layer 212 which is skin-contacting is approximately 100%. However, where the patch is constructed as a bandage (as discussed hereinafter), the skin-contacting portion is less, as accommodation must be made for a central wound-contacting absorbent pad. At least one reservoir 220 containing a scent is disposed in the backing layer 212. Reservoir 220 may be constructed as at least one pocket integrated within the backing layer 212. Preferably, reservoir 220 is provided as a plurality of reservoirs 220 constructed as pockets 221, as shown in FIGS. 1a-1c. In a second embodiment, pluralities of reservoirs 220 are provided, constructed as microcapsules 223, admixed with an adhesive 215 coated on backing layer 212.

The reservoirs 220 or microcapsules 223 as herein shown, are operative to rupture upon application of pressure or scratching by the patch wearer, thereby releasing the scent. Upon release scent is delivered to the skin of the patch wearer for emanating the scent. The scent is preferably a perfume composed of a mixture of fragrant essential oils and aroma compounds, fixatives, and solvents used to give the human body, animals, objects, and living spaces a "pleasant" smell.

The microcapsules 223 are generally small in diameter and contain only a small volume of the scent or perfume. The perfume spreads approximately a few times the diameter of each microcapsule. However, there are many microcapsules, nearly uniformly distributed in the adhesive layer. The appropriate measure of scent is its overall volume, as compared to the volume of the adhesive used. The scent volume is typically present in the range of about 5 to 20% of the volume of the adhesive used. In this manner, the adhesive contains the microcapsules, with the sent nearly uniformly distributed, and affords sufficient volumetric release of the scent for effective aroma emission. The scent or perfume may be contained in microcapsules of polymeric or gelatin composition. Use of gelatin, which dissolves in water, is not a problem when the adhesive used is water resistant.

The method of manufacture of the microcapsules is well known in the art and includes formation of polymeric bubbles that contain the scent or perfume. For example, soybean oil can be easily micro encapsulated in the reaction product of ethylene diamine and toluene diisocyanate. Techniques for producing microcapsules are detailed in 'Microcapsules and other capsules-Advances since 1975', edited by M. H. Gutcho, 1979 published by Noyes Data Corporation, the disclosure of which is specifically incorporated herein by reference thereto.

Figure 4A:
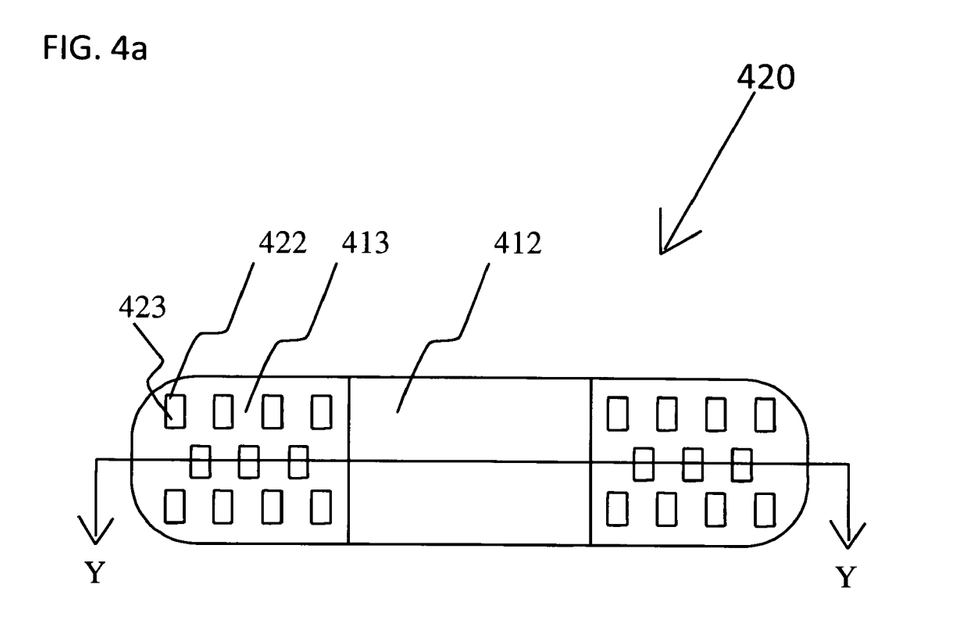
FIG. 4a is a schematic diagram of an embodiment of the invention depicting the front view of scent emitting patch and/or bandage with pockets of scents contained within the backing layer of the adhesive coated end tabs of a bandage.

FIG. 4a shows generally at 420 a schematic diagram of the first embodiment of the invention depicting the front view of a scent emitting bandage with a wound contacting central pad 412 and adhesive coated end tabs 413 that attach the bandage to the skin. The end tabs 413 have a plurality of pockets 422 which contain a scent or perfume 423. The pockets will be covered by the adhesive on the skin contacting side. They are preferably buried within the backing layer and will not be visible. Pockets 422 are shown in the drawing for clarity.

Figure 4B:
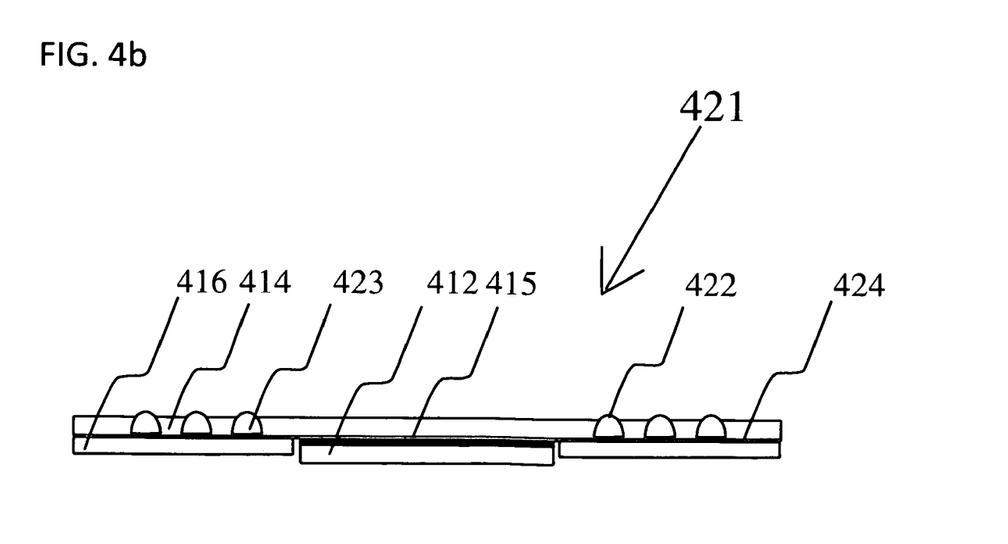

FIG. 4b shows generally at 421 a schematic diagram of the cross section of a bandage of the first embodiment of the present invention, taken along the line YY of FIG. 4a. The wound contacting central pad 412 is bonded to the backing layer 414 with hot melt or other permanent adhesive 415. The backing layer 414 contains pockets 422, which contain scent 423. The backing layer 414 is sealed with a second polymeric sheet 424. The adhesive layer 416 coats the second polymeric sheet 424.

Figure 5A:
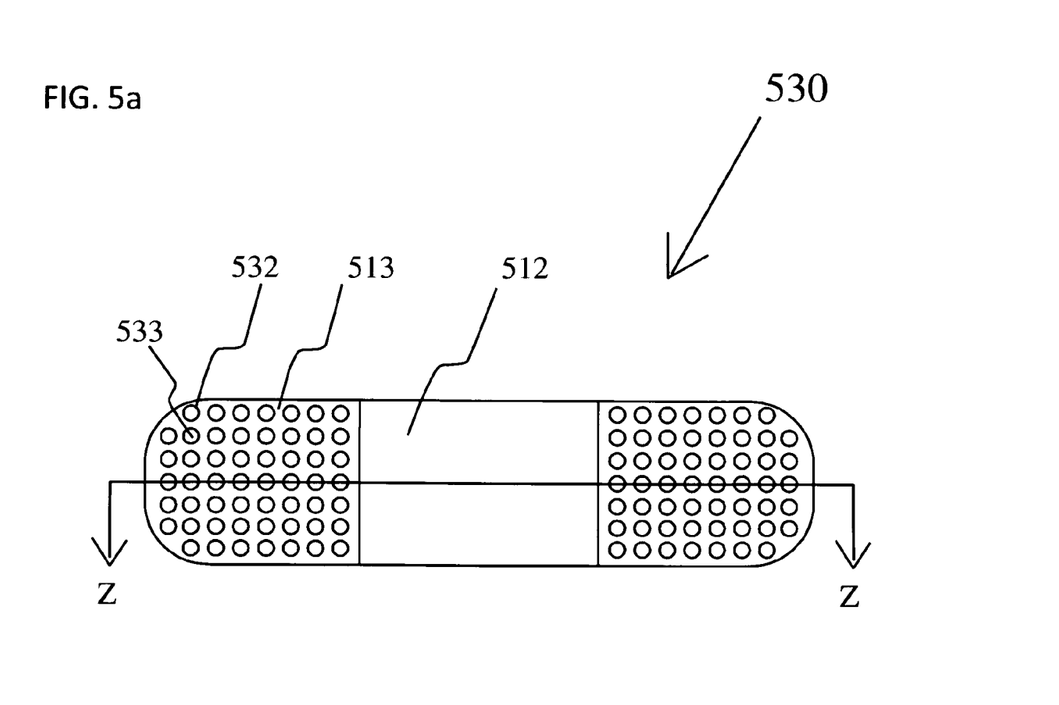
FIG. 5a is a schematic diagram of another embodiment of the invention depicting the front view of a scent emitting patch and/or bandage with scents contained in the form of microcapsules that are present within the adhesive layer of the end tabs of a bandage.

FIG. 5a shows at 530 a schematic diagram of the second embodiment of the invention illustrating the front view of a bandage with wound contacting central pad 512 and adhesive coated end tabs 513 that attach the bandage to the skin. The adhesive contains a plurality of microcapsules 532 that contain the scent/perfume 533 within the adhesive layer 516 of the bandage's adhesive coated end tabs 534. The microcapsules will be generally invisible, since they are contained within the adhesive coating of the end tabs. They are shown for clarity.

Figure 5B:
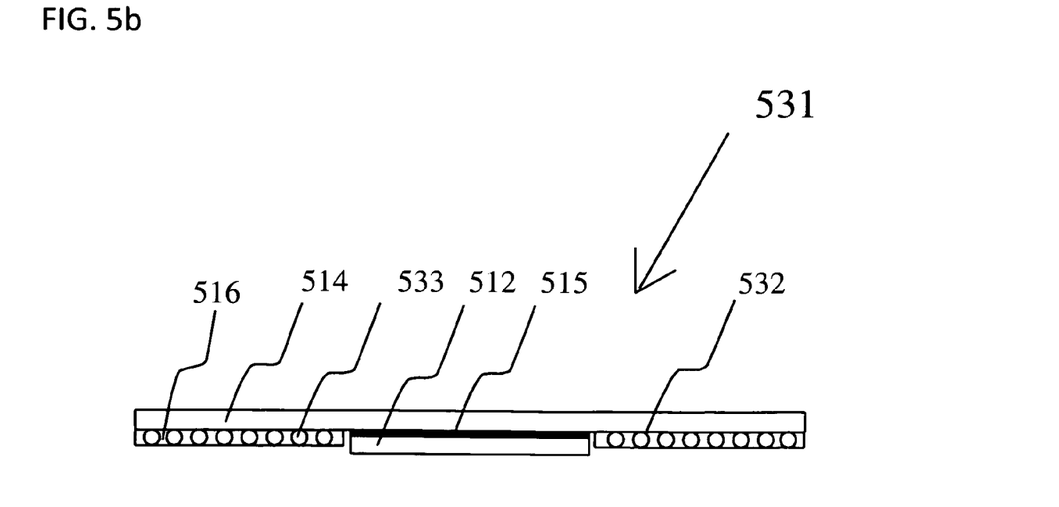

FIG. 5b shows at 531 a schematic diagram of the cross section of a bandage according to the second embodiment of the invention, taken along line ZZ of FIG. 5a. The wound-contacting central pad 512 is bonded to the backing layer 514 with hot melt or other permanent adhesive 515. The backing layer 514 has a coating of adhesive 516 in the skin contacting areas of the bandage, which contains microcapsules 532 with scent/perfume 533.

The key features of the scent emitting patch and/or bandage include, in combination, the features set forth below:
1. a bandage having a backing layer;
2. the backing layer having a plurality of portions coated with adhesive for attachment to skin;
3. optionally the backing layer having a central portion permanently attached to an absorbent pad;
4. the backing layer comprising individually separated or interconnected pockets of scent comprising a perfume or microcapsules containing a scent; and
5. application of pressure to or scratching the outer surface of the backing layer being operative to break the pockets or microcapsules, thereby releasing the scent at the skin-contact or skin-adhesive interface.

The scent emitting patch and/or bandage disclosed herein can be modified in numerous ways without departing from the scope of the invention. For example, different patch or bandage geometries, diverse dispersions of scent reservoirs/compartments, and a variety of release methods may be used. These and other modifications are intended to fall within the scope of the invention, as defined by the subjoined claims.

Having thus described the invention in rather full detail, it will be understood that such detail need not be strictly adhered to, but that additional changes and modifications may suggest themselves to one skilled in the art, all falling within the scope of the invention as defined by the subjoined claims.

What is claimed is:
1. A scent emitting patch, comprising:
   a. an external top layer and a backing layer having a skin-contacting segment opposite the external top layer appointed for contact with skin of a patch wearer;
   b. at least one portion of said skin contacting segment of said backing layer having an adhesive;
   c. a plurality of reservoirs being disposed in the backing layer, said reservoirs containing a scent, wherein said backing layer is constructed from a first and second polymeric sheets, the first polymeric sheet having formed in it said plurality of reservoirs constructed as pockets and a second polymeric sheet, which is generally thinner and has a lower strength than said first polymeric sheet, spread over said first polymeric sheet covering and sealing said pockets;
   d. said pockets at second polymeric sheet being operative to rupture upon application of pressure or scratching by said patch wearer, thereby releasing said scent;
   e. said scent, upon release being delivered to said skin of said patch wearer for emanating said scent;
   f. a central wound-contacting absorbent pad bonded by hot melt glue or strong adhesive to said backing layer; and
   g. said external top layer including at least one portion having a plurality of apertures integrated therein and located in alignment with each of said reservoirs containing said scent disposed in said backing layer.

2. A scent emitting patch as recited by claim 1, wherein said adhesive is selected from a group comprising acrylic based, dextrin based, and urethane based adhesives, and adhesives based on natural and synthetic elastomers.

3. A scent emitting patch as recited by claim 1, wherein said scent is a perfume.

4. A scent emitting patch as recited by claim 1, wherein said plurality of reservoirs are individually separated from one another.

5. A scent emitting patch as recited by claim 1, wherein said plurality of reservoirs are interconnected with one another.

6. A scent emitting patch as recited by claim 1, wherein said plurality of reservoirs containing said scent are disposed within said skin-contacting segment of said backing layer.

7. A scent emitting patch as recited by claim 1, wherein said plurality of reservoirs containing said scent are disposed in said adhesive-containing portions of said backing layer.

8. A scent emitting patch as recited by claim 1, wherein said pockets have a volume of said scent ranging from about 0.01 cc to 0.5 cc and said pockets are spaced apart by a distance ranging from about 0.01 cm to 0.2 cm.

9. A scent emitting patch as recited by claim 1, wherein said plurality of reservoirs contain about 5 to 20 percent scent by volume.

10. A scent emitting patch as recited by claim 1, wherein said plurality of portions of said skin-contacting segment of said backing layer containing said adhesive is located along an outer perimeter of said back layer.

11. A scent emitting patch as recited by claim 1, wherein said plurality of portions of said skin-contacting segment of said backing layer containing said adhesive is located along two parallel side perimeters of said back layer.

12. A scent emitting patch as recited by claim 1, wherein said external top layer is opaque.

13. A method for producing a scent emitting patch, comprising the steps of:
   a. selecting a first polymeric layer;
   b. embossing said first polymeric layer to form a plurality of pockets therein;
   c. filling said pockets with a scent;
   d. selecting a second polymeric layer, which is generally thinner and has a lower strength than said first polymeric layer;
   e. spreading said second polymeric layer over said first polymeric layer to cover said filled pockets;
   f. bonding said second polymeric layer to said first polymeric layer to form filled pockets of said scent, wherein said first polymeric layer and second polymeric layer together construct a backing layer having at least one skin contacting segment appointed for contact with skin of patch wearer;
   g. applying skin-contacting adhesive at least one portion of a skin-contacting segment of said backing layer, whereby release of said scent can be triggered when said wearer applied pressure to or scratches said backing layer, causing rupture of said pockets at the second layer, said scent, upon release being delivered to said skin of said patch wearer for emanating said scent;
   h. bonding a central wound-contacting absorbent pad by hot melt glue or strong adhesive to said backing layer; and
   i. providing an external top layer, opposite said skin contacting segment of said backing layer, including at least one portion having a plurality of apertures integrated therein and located in alignment with each of said pockets containing said scent disposed in said backing layer.

* * * * *